(12) United States Patent
Engler et al.

(10) Patent No.: US 6,743,893 B2
(45) Date of Patent: Jun. 1, 2004

(54) RECEPTOR-MEDIATED UPTAKE OF PEPTIDES THAT BIND THE HUMAN TRANSFERRIN RECEPTOR

(75) Inventors: Jeffrey A. Engler, Birmingham, AL (US); Jae Hwy Lee, Seoul (KR); James F. Collawn, Birmingham, AL (US); Bryan A. Moore, Palatine, IL (US)

(73) Assignee: The UAB Research Foundation, Birminghan, AL (US)

( * ) Notice: Subject to any disclaimer, the term of this patent is extended or adjusted under 35 U.S.C. 154(b) by 174 days.

(21) Appl. No.: 09/995,804

(22) Filed: Nov. 29, 2001

(65) Prior Publication Data

US 2002/0115824 A1 Aug. 22, 2002

Related U.S. Application Data

(60) Provisional application No. 60/253,940, filed on Nov. 30, 2000.

(51) Int. Cl.[7] .............................. C07K 7/00; C07K 1/00; A61K 38/00

(52) U.S. Cl. .............................. 530/300; 514/2; 530/350
(58) Field of Search .................................. 530/300, 350; 514/2; 424/1.65, 9.1

(56) References Cited

PUBLICATIONS

WO200164835, Tang et al., Sep. 7, 2001, relevant pp. 1–98, 618, 1396–1399; SEQ ID No.:15308, see alignment.*

* cited by examiner

*Primary Examiner*—Gary Kunz
*Assistant Examiner*—Sharon Turner
(74) *Attorney, Agent, or Firm*—Glenna Hendricks; Lucy Hicks

(57) ABSTRACT

Peptides have been discovered which are capable of binding to and internalizing with the human transferrin receptor (hTfR). The sequences HAIYPRH (Seq. ID No. 1) and THRPPMWSPVWP (Seq. ID No. 2) are capable of binding to and internalizing with the human transferrin receptor. When these molecules were fused with other molecules, the fusion product was internalized in cells expressing hTfR. The sequences have use for targeting other peptides and proteins into cells expressing hTfR.

7 Claims, No Drawings

RECEPTOR-MEDIATED UPTAKE OF PEPTIDES THAT BIND THE HUMAN TRANSFERRIN RECEPTOR

This application takes priority from U.S. Provisional patent application 60/253,940, filed Nov. 30, 2000.

This work was supported by USPHS grants R01HL58339 and IP50 DE/CA 11910 and by NCI grant CA-13148. Hence, the United States Government has certain rights in this invention.

FIELD OF THE INVENTION

This invention relates to use of peptides which target the human transferrin receptor. Peptides of the invention can be used to direct other peptides, proteins and other diagnostic or therapeutic agents into cells for both diagnostic and therapeutic purposes.

BACKGROUND OF THE INVENTION

Previous work relating to redirecting viral vectors in gene therapy by using short peptide ligands to redirect virus particles to specific cell types are known. One of the limitations of this strategy is that short peptide sequences that bind efficiently to cell surface receptors on specific cell types must be identified. One experimental approach to identify such short peptides that holds promise is bacteriophage display.

For more than a decade, phage display has exploited the physical linkage between random peptide sequences expressing on phage and the DNA encoding that sequence. This linkage allows for rapid identification of peptide ligands. A random peptide sequence is expressed as a fusion with a bacteriophage coat protein and is available for testing as a ligand for various targets. Phage display has successfully been used to identify single chain antibodies with specificity for various biological molecules. Phage display strategies can be used to elucidate the amino acids responsible for protein—protein interactions, to find organ-specific phage, and to find substrate recognition sequences for enzymes. The process of using multiple rounds of phage display to enrich for a particular sequence is called biopanning.

The human transferrin receptor (hTfR) has been studied extensively as a model system for receptor-mediated endocytosis, a marker for cellular proliferation, and a target for therapeutics. The hTfR is ubiquitously expressed and over-expressed at least 100 fold in oral, liver, pancreatic, prostate and other cancers. This increase in transferrin receptor (TfR) in cancers has been attributed to the increased metabolism of these transformed cells, making the hTfR a useful diagnostic marker. Because of its expression pattern and pathway characteristics, the hTfR is an attractive target for therapeutics. The TfR is a dimer composed of two identical 95 kDa subunits and is responsible for the majority of cellular iron uptake. The type II cell surface receptor binds 80 kDa transferrin (Tf) and the complex is internalized through clathrin-coated pits. Iron is released from transferrin in the acidic early endosome and the apotransferrin-receptor complex is recycled back to the cell surface where apotransferrin is recycled.

A blast search failed to yield any significant homologies between either HAIYPRH (Seq. ID No. 1) or THRPPMWSPVWP (Seq. ID No. 2) to known proteins, including Tf.

SUMMARY OF THE INVENTION

This invention relates to peptides which are capable of binding to and internalizing with the human transferrin receptor (hTfR). The sequences HAIYPRH (Seq. ID No. 1) and THRPPMWSPVWP (Seq. ID No. 2) are capable of binding to and internalizing with the human transferrin receptor. When these molecules were fused with other molecules, the fusion product was internalized in cells expressing hTfR. The sequences have use for targeting other peptides and proteins into cells expressing hTfR. The phage display system using whole cell selective biopanning could also be applied to find small ligands for other cell surface receptors. This sequence is not found in human transferrin protein. Furthermore, this sequence does not compete with transferrin itself for binding to the hTfR.

DETAILED DESCRIPTION OF THE INVENTION

It is important that easily produced peptides that can facilitate entry of diagnostically and therapeutically useful peptides and proteins into cells having particular characteristics be available. The identification of peptides that will facilitate entry of such peptides into cells which are more likely to be aberrant has particular use. The peptides of the invention are useful for facilitating entry of diagnostically and therapeutically useful agents, including peptides and proteins. Since malignant cells produce increased expression of hTfR, the peptides, HAIYPRH (Seq. ID No. 1) and THRPPMWSPVWP (Seq. ID No. 2), are particularly useful for study and treatment of malignancies.

A phage display selection strategy was utilized that resulted in identification of the peptides. This selection system is based on alternating rounds of negative selection on chicken embryo fibroblast (CEF) cells lacking hTfR and positive selection on chicken embryo fibroblast cells expressing hTfR (CEF+hTfR). Biopanning on whole cells was exploited to select the peptides HAIYPRH (Seq. ID No. 1) and THRPPMWSPVWP (Seq. ID No. 2). These peptides were able to target a macromolecule to and internalize through the hTfR, as was demonstrated by phage binding, competition and immunofluorescence studies. It was also shown that these two peptides bind sites that do not overlap with the native ligand, transferrin, indicating they could be used in vivo for targeting macromolecules to the endocytic pathway in hTfR-positive cells.

The biopanning procedure could be applied to find small peptide ligands for other cell surface receptors. There is a great need to find new epitopes on various cancer cell types for diagnostic purposes. The subtractive method of biopanning disclosed herein would be useful for finding new cell surface markers. Biopanning on whole cells can be especially useful in situations where the receptor can not be purified or does not maintain its native confirmation when isolated.

Materials and Methods:

Cell lines: The two chicken embryo fibroblast cell lines, CEF and CEF+hTfR, used for selective biopanning, were described previously (Collawn, et al, *Cell,* 63, 1061–1072 (1990) and Odorizzi, et al., *J. Cell Biol.,* 126, 317–330 (1994)). Chicken embryo fibroblasts have been used extensively for study of hTfR. The native cells express chicken transferrin receptors, but this receptor cannot bind human transferrin. Two cell lines were previously established through stable transduction with retroviral vectors to yield CEF and CEF+hTfR cells. CEF cells do not express the human transferrin receptor. CEF+hTfR cells constitutively express hTfR. Protein expression of hTfR by CEF cells was periodically checked by $^{125}$I-Tf binding. Both cells are grown in monolayer cultures in Dulbecco's Modified Eagle Medium supplemented with 1% chicken serum, 1% bovine calf serum, 1% L-glutamine 200 nM, and 2% tryptose phosphate and maintained at 37° C. in 13% $CO_2$.

Antibodies: Monoclonal anti-GFP (green fluorescent protein) antibody (Clontech, Palo Alto, Calif.) was used for Western blot analysis and immunofluorescence at 1:5,000 and 1:250 dilution, respectively. Horse radish peroxidase conjugated goat anti-mouse antibody (Pierce, Rockford, Ill.), Oregon-Green and Texas-Red secondary antibodies (Molecular Probes, Eugene, Oreg.) were used at 1:10,000, 1::250, 1:250 dilution, respectively.

Electrophoretic Methods: Samples were dissolved on SDS-PAGE gels by the methods of Laemmli and transferred to nitrocellulose membrane by electroblotting for Western blot analysis (Laemmli, U.K, Nature, 227, 680–685). The membranes were blocked with 5% milk in tris buffered saline with 1% Trition X-100 (TBS-TX) (50 mM Tris-HCL, pH 7.5, 0.2 M NaCl, 1% Triton X-100), and incubated with primary antibody in TBS-TX with 2.5% milk overnight at 4° C. The membranes were then washed in TBS-TX and incubated with peroxidase-conjugated secondary antibody and developed with the enhanced chemiluminescence (ECL) kit in accord with the manufacturer's instructions (Amersham Pharmacia Biotech, Buckinghamshire, England).

Biopanning: Ph.D.-7™ or Ph.D.-12™ Phage Display Peptide Library Kit (New England Biolabs, Inc, Bevery, Mass.) was used for biopanning on CEF and CEF+hTfR cells. The Ph.D.™ phage display peptide library is based on a combinatorial library of random 7 or 12 amino acid peptides fused to a minor coat protein of the filamentous coliphage M13. In separate studies, two different phage display peptide libraries were used to select for 7-mer and 12 mer peptide sequences that could bind the hTfR expressed on the surface of CEF+hTfR cells. Cells were washed and incubated in serum-free opti-MEM (Gibco BRL Life Technologies, Gaithersburg, Md.) at 37° C. for 1 hour prior to all biopanning procedures. Phage binding was carried out at 4° C. in serum-free Opti-MEM with 1×10⁶ cell/3.5 cm well. Initial biopanning procedures applied $2 \times 10^{11}$ phage to CEF cells for two hours; unbound phage were transferred to CEF+hTfR cells for 1 hour. Cells were washed 10 times with Opti-MEM, and bound phage was quickly eluted with low pH buffer (0.2 M glycine-HCL, pH 2.2) and neutralized with 1M Tris-HCl, pH 9.1. Eluted phage were amplified in 20 ml Luria-Bertani medium (LB) containing E. coli ER2537 (for 7-mer phage) and ER2783 (for 12-mer phage) at 37° C. Phage from liquid cultures were obtained by clearing the supernatant twice by centrifugation at 10,000 rpm for 15 minutes at 4° C., and precipitated with 1/6 volume of PEG/NaCl (10% polyethylene glycol-8000, 2.5M NaCl) at 4° C. overnight. Phage pellets were suspended in 1 ml TBS (50 mM Tris-HCl, 150 mM NaCl), and precipitated with PEG/NaCl for 1 hour. Amplified phage were resuspended with 200 µl TBS, 0.02% $NaN_3$, and these amplified phage were used for additional rounds of biopanning. After each round of biopanning, the final elutes were titrated, amplified in E. coli, and plated onto LB plates. The plates were incubated at 37° C. overnight. Individual plaques were subjected to plaque amplification, DNA purification, and DNA sequencing using a modified Sanger sequencing reaction (Sanger, et al., Pro Natl Acad Sci USA, 74, 5463–5467 (1977)) with the appropriate sequencing primers.

```
7-mer sequencing primer:   5'-TGGGATTTTGCTAAAAAC-3'      (Seq. ID No. 5)

12-mer sequencing primer:  5'-GTATGGGATTTTGCTAAACAAC-3'  (Seq. ID No. 6)
```

Peptide Synthesis: The peptides HAIYPRH (Seq. ID No. 1), IRHPHYA (Seq. ID No. 3), THRPPMWSPVWP (Seq. ID No. 2), and PWRPSHPVWMPT (Seq. ID No. 4) were synthesized on an Applied Biosystems Model 440 by means of the solid phase peptide synthesis procedure at the Peptide Synthesis Core Facility of the University of Alabama at Birmingham (UAB) Comprehensive Cancer Center. These peptides were purified by high pressure liquid chromatography, and the molecular weights were confirmed by mass spectrometry.

Binding and Competition Studies: Purified phage populations were amplified and were verified to be homogenous through DNA sequencing. Cells were prepared for binding as was described for biopanning procedures. Preparations of plaque-purified and titered phage ($1 \times 10^{11}$) were incubated in serum-free Opti-MEM on either CEF or CEF+hTfR cells at 4° C. for 1 hour. The cells were washed repeatedly with Opti-HEM and bound phage were eluted with low pH buffer and subsequently titered. In competition studies, holo-transferrin (Calbiochem, La Jolla, Calif.) or synthesized peptides were added to CEF+hTfR cells prior to addition of the phage for 1 hour at 4° C. Multiple trials were completed and average titers and standard deviations determined. The titers determined on CEF+hTfR cells were divided by the titers determined on CEF cells and multiplied by 100 to yield fold over control data points.

Modified GFP Constructs: Transferrin from human serum, bovine serum albumin (BSA), and purified wild-type GFP (wtGFP) were obtained from Sigma (St. Louis, Mo.) and Clontech (Palo Alto, Calif.), respectively. The tagged GFP genes were generated by the PCR with template DNA Clontech's GFP vector. The PCR reactions were carried out in a Perkin Elmer Cetus DNA Thermal Cycler for 30 cycles of 95° C., 1 minute; 55° C., 1 minute; and 72° C., 1 minute.

```
HAIYPRH (Seq ID No. 1)-taged GFP PCR oligonucleotides were:
Upstream:   5'-TCTAGATCTGATGAGTAAAGGAGAAGAA-3'                                    (Seq. No. 7)

Downstream: 5'-TTAAAGCTTTTAATGGCGCGGATAGATCGCATGTTTGTAGAGCTCATCCATGCC-3'         (Seq. No. 8)

THRPPMWSPVWP (Seq ID No. 2)-tagged GFP PCR oligonucleotides were:
Upstream:   5'-TCTAGATCTGATGAGTAAAGGAGAAGAA-3'                                    (Seq. No. 7)

Downstream: 5'-TAAAGCTTTTACGGCCACACCGGGCTCCACATCGGCGGGCGGTGGGTTTTGTAGAGCTCATCCATGCC-3'  (Seq. No. 9)
```

The PCR products were purified with the Qiagen Gel Extraction Kit (Qiagen, Valencia, Calif.) and cut with BcrlII and HindIII restriction enzymes (Roche, Nutley, N.J.), and subcloned into the pET-32a(+) bacterial expression vector (Novagen, Madison, Wis.). The resulting expression vector was verified using a modified Sanger sequencing method. The tagged GFP expression plasmids were transformed into BL21/DE3 *E. coli* and expression was induced for 3–4 hours with 1 mM isopropyl-β-D-thioglactopyranoside (IPTG) when the culture O.D.,$_{600}$=0.5. Cells were pelleted, then resuspended in phosphate buffer with 20 mM imidazole followed by passage through a French press at 10,000–15,000 psi. Cell lysates were passed over a PisTrap nickel column (Amersham Pharmacia Biotech, Piscataway, N.Y.). The column was washed and finally eluted using an imidazole gradient. The purified protein was assayed by SDS-PAGE followed by Coomassie staining and Western blot analysis with a GFP monoclonal antibody (Clontech). ECL development was carried out as per the manufacturer's instructions (Amersham Pharmacia Biotech). Protein concentrations were determined with the Bio-Rad Protein Assay kit (Bio-Rad Laboratories, Hercules, Calif.).

Immunofluorescence: CEF+hTfR cells were grown on glass coverslips to 50% to 75% confluence. The coverslips were washed and incubated in serum-free Opti-MEM media at 37° C. for 1 hour. Then 2 µg of wild-type GFP (Clontech), HAIYPRH (Seq. ID No. 1)-tagged GFP, THRPPM-WSPVWP (Seq. ID No. 2)-tagged GFP, or Texas-Red Tf (Molecular Probes) was applied to cells in serum-free Opti-MEM media for 1 hour at 4° C. or 37° C. Cells were washed with Opti-MEM, then fixed in 3% formaldehyde for 30 minutes at 4° C. Alternatively, the cells were acid-washed with 0.2 M glycine-HCl, Ph 2.2, prior to fixation. A GFP monoclonal antibody (Clontech) was used in conjunction with an Oregon-Green Goat Anti-Mouse (Molecular Probes) to augment GFP fluorescence. All slides were counterstained with DAPI (2(4Amidinophenyl)-6indole carbamidinedihydrochioride) (Sigma). The microscopic slides were mounted in Prolong™ antifade medium (Molecular Probes). Images were captured on an AX70 microscope with Olympus Camera (Olympus, Melville, N.Y.) and analyzed with ESPRIT software (Life Science Resources, Cambridge, England). Final figures were assembled using Microsoft Power Point (Microsoft Corp., Redmond, Wash.). For colocalization studies, CEF+hTfR were incubated with 2 µg/ml GFP fusion protein and 2 µg/ml of Texas-Red Tf for 1 hour and processed as described above.

Standard Analysis: Purified proteins (transferrin, wtGFP, GFP-HAIYPRH (Seq. ID No. 1) and GFP-THRPPMWSPVWP (Seq. ID No. 2) were labelled with $^{125}$I to a specific activity of 1–2 µCi/µg with CPM/µg determined by a gamma counter and Bradford assay. CEF+hTfR cells were plated in duplicate at a density of 7.5×10$^4$ cells/well in 24 well dishes and grown overnight. Cells were washed and incubated in serum-free Opti-MEM for 1 hour at 37° C. Cells were placed on ice with the various amounts of labelled protein in a total of 200 µl of cold 0.1% BSP in phosphate buffered saline (PBS). After 1 hour, the unbound protein was removed and cells were washed 4 times with 0.1% BSA in PBS. 1M NaOH was added to lyse the cells for determining the bound fraction. Both unbound and bound fractions were counted in a gamma counter and binding affinities were determined using Scatchard analysis. Studies were repeated 3 times and yielded comparable binding affinities for all proteins tested.

EXAMPLE 1

The biopanning procedure with chicken embryo fibroblast cells was performed as described above. The procedure used both negative and positive binding steps to isolate specific peptide sequences that bind the hTfR.

After the cells were incubated in serum-free media Opti-MEM at 37° C. for 1 hour to remove Tf found in the serum, ice-cold serum-free Opti-MEM media was applied and the cells were held at 4° C. throughout the selected process to prevent internalization of the receptor. The original phage library containing 2×10$^{11}$ phage was applied to CEF cells for 2 hours. Unbound phage were transferred to another well of CEF cells for an additional hour, before transferring the unbound phage to a well of CEF+hTfR cells. After extensive washing, the bound phage were removed with low pH buffer and subsequently neutralized. The eluted phage were titered and amplified in *E. coli*. After each amplification step multiple plaques were selected for sequencing. The amplified eluted phage were applied to CEF cells to begin the biopanning process again. This cycle was carried out 10 rounds for the 7-mer peptide library and 7 rounds for the 12-mer peptide library to achieve significant enrichment of a single sequence above all others. Sequencing of individual phage plagues allowed for the monitoring of sequence convergence during multiple rounds of biopanning. Phage titers of total phage eluted were determined and were noticed to increase after each round of biopanning. The most prominent sequence selected from the 7- mer library was HAIYPRH (Seq. ID No. 1) (7-mer) while the 12- mer library converged to the sequence of THRPPMWSPVWP (Seq. ID No. 2) (12-mer). There were no other sequences that arose consistently throughout the biopanning procedure.

Phage that did not bind the CEF cells were applied to CEF+hTfR cells and the bound phage were eluted with low pH buffer. The eluted phage were amplified for additional rounds of biopanning. Between each round, the phage were titered and sequenced to monitor convergence of sequence.

EXAMPLE 2

As an initial test to determine whether the isolated phage bound to hTfR, a phage binding study was performed. Homogeneous pools of five different isolates from the 7-mer phage and five isolates from the 12-mer phage were each amplified, purified and verified by DNA sequencing. Individually, 10$^9$ phage were applied to CEF or CEF+hTfR cells. Phage were bound to CEF or CEF+hTfR cells for 1 hour at 4° C., then washed extensively with Opti-MEM to remove unbound phage. Bound phage were eluted with low pH buffer, neutralized, and titered on a lawn of *E. coli*. Titering each phage on both cell types was repeated three times, and average titers and standard deviations were determined. Considering the 7-mer sequences, it was found that significantly higher titers were obtained only with HAIYPRH (Seq. ID No. 1) phage bound to CEF+hTfR cells when compared to other phage tested. In studies relating to the 12-mer sequences, it was found that the THRPPM-WSPVWP (Seq. ID No. 2) phage had higher titers on CEF+hTfR cells than the other 12 amino acid phage tested. On CEF cells, which do not express hTfR, all phage tested bound at the same low efficiency. A low level of non-hTfR dependent binding is expected, due to interactions between phage coat proteins and the various proteins on the surface of chicken embryo fibroblast cells. Titering studies demonstrated that phage containing either peptide sequence HAIYPRH (Seq. ID No. 1) or THRPPMWSPVWP (Seq. ID No. 2) bound CEF+hTfR cells more efficiently than any other phage tested and that this higher binding depends on the presence of human transferrin receptor.

EXAMPLE 3

Competition studies were conducted to determine whether the two phages bound the same region of the hTfR as serum Tf itself. It was found that the titers of HAIYPRH (Seq. ID No. 1) or THRPPMWSPVWP (Seq. ID No. 2) phage bound to CEF+hTfR cells in the presence of various added peptides or Tf were significant. The HAIYPRH (Seq. ID No. 1) phage was competed away to background levels only by the HAIYPRH (Seq. ID No. 1) peptide and not by the scrambled sequence of IRHPHYA (Seq. ID No. 3). The 12-mer THRPPMWSPVWP (Seq. ID No. 2) phage was only competed by the THRPPHWSPVWP (Seq. ID No. 2) peptide and not by the scrambled 12-mer sequence PWRPSH-PVWMPT (Seq. ID No. 4). Other peptides tested failed to compete away the phage from binding the cells. Interestingly, the binding of either phage was unaffected by the presence of Tf, suggesting that each phage sequence has a different binding site on the hTfR. Due to a synthesis error, a peptide with the sequence HAIYPNH (Seq. ID No. 14) was also synthesized. Competition studies were completed with this peptide which disclosed no effect on the HAIYPRH (Seq. ID No. 1) phage binding. The result suggests that the 7-mer phage binding depended on the arginine in the original HAIYPRH (Seq. ID No. 1).

EXAMPLE 4

To evaluate the sufficiency of capacity of the peptides to mediate uptake of carrier protein, GFP fusion proteins were prepared. Immunofluorescence was used to determine if the GFP-peptides fusion constructs were internalized using the following assay. GFP-peptide constructs were cloned with a C-terminal peptide addition of either HAIYPRH (Seq. ID No. 1) (GFP-HAIYPRH) or THRPPMWSPVWP (Seq. ID No. 2) (GFP-THRPPMWSPVWP). These constructs were expressed and purified to greater than 95% by Coomassie staining. Purified proteins were applied to CEF+hTfR cells at 4° C. (which prevents endocytosis) or at 37° C. Cells were washed with Opti-MEM, fixed and processed as described under the Materials and Methods section above. Alternatively, the cells were washed with low pH buffer prior to fixation. This acid wash determined whether the protein was endocytosed by removing proteins bound at the cell surface.

Immunofluorescence microscopy was used to follow binding and internalization of the wtGFP, GFP fusion proteins and transferrin to CEF+hTfR cells. Wild-type GFP was used as a negative control, while Tf conjugated to the Texas-Red fluorochrome was used as a positive control. The conjugation of Texas-Red to Tf has been shown previously not to diminish interaction with the hTfR. In all studies, cell nuclei were counterstained with DAPI.

Immunofluorescence images of the localization of various proteins applied to CEF+hTfR cells at either 4° C. or 37° were studied. At 4° C., endocytosis was blocked so that all proteins remain at the cell surface, and an acid wash removes all cell surface bound proteins. When immunofluorescence of the various proteins was studied on CEF+hTfR cells which had been incubated at 37° C. for one hour, localization of GFP-HAIYPRH (Seq. ID No. 1), GFP-THRPPHWSPVWP (Seq. ID No. 2) or Texas-Red.Tf was found on cells that had not been exposed to acid wash. The total fluorescence shown could result from both cell surface and endocytosed proteins. There was minimal binding of wtGFP even without an acid wash.

The cells that had undergone a low pH buffer wash to enable identification of proteins that had been endocytosed were evaluated. While wtGFP was unable to be endocytosed into CEF+hTfR cells, both GFP-HAIYPRH (Seq. ID No. 1) and GFP-THRPPMWSPVWP (Seq. ID No. 2) showed a speckled pattern of fluorescence typical of endocytosed ligands. The Texas-Red Tf was readily endocytosed into the CEF+hTfR cells and produced a spotted pattern similar to that seen with the two GFP fusion proteins.

In separate studies at 4° C. or 37° C., CEF cells were used for immunofluorescence binding assays and neither of the GFP fusion proteins or transferrin bound or internalized these cells, as was expected, since these CEF cells lack the hTfR. Immunofluorescent internalization studies were also performed with Hela cells and yielded identical result to CEF+hTfR cells.

EXAMPLE 5

The phage titering experiments demonstrated that neither peptide sequence competed with Tf or hTfR binding. Co-localization studies were conducted with both GFP-Peptide and Texas-Red Tf constructs. Cells were incubated at 37° C. for 1 hour with Texas-Red Tf and either GFP-HAIYPRH (Seq. ID No. 1) or GFP-THRPPMWSPVWP (Seq. ID No. 2). Cells were acid washed immediately, fixed and stained with DAPI. Images were captured using the appropriate filter and overlaid with images captured with the DAPI filter. Merging GFP, Texas-Red Tf and DAPI images yielded the co-localization images. The fluorescent patterns of the GFP fusion proteins and Tf were identical after acid wash. This result indicated that the GFP-peptides were internalized and bound in the same intracellular compartment as Tf.

EXAMPLE 6

Purified transferrin, wtGFP, GFP-HAIYPPH (Seq. ID No. 1) and GFP-THRPPMWSPVWP (Seq. ID No. 2) were labelled with $^{125}$I on tyrosine residues to a specific activity of 1–2 $\mu$Ci/$\mu$g. Serial dilutions of labelled proteins were incubated with CEF+hTfR cells on ice in PBS-0.1% BSA in duplicate wells. After 1 hour, the unbound fraction was removed and cells were washed four times. Cells were removed from the well with 1N NaOH. The unbound and bound fractions were counted in a gamma counter and fmoles of bound and unbound were calculated. Scatchard plots were derived by plotting bound versus bound/free of an average value generated by the duplicate wells. A best of fit line was generated using the Excel program (Microsoft Corp.) and the binding affinities were determined by the slope of the plotted lines. Repetitive trials produced comparable binding affinities. The affinity of Tf was found to be $2.7 \times 10^{-9}$, similar to previous reports. The affinity for wtGFP and GFP-HAIYPRH (Seq. ID No. 1) were determined to be nominal at $2.4 \times 10^{-4}$M and $3.6 \times 10^{4}$M, respectively. This low affinity of GFP-HAIYPRH (Seq. ID No. 1) was attributed to the $^{125}$I labelling of the tyrosine residue in the peptide, which could block this peptide's interaction with the hTfR. However, GFP-THRPPMWSPVWP (Seq. ID No. 2) was shown to have $2.3 \times 10^{-8}$M affinity for CEF+hTfR cells, indicating that its affinity was only 10-fold lower than the native Tf ligand.

Peptides containing the sequences HAIYPRH (Seq. ID No. 1) and THRPPMWSPVWP (Seq. ID No. 2) can be used to target viral vectors, as well as proteins, to the endocytic pathway via the hTfR. Competition studies suggest that transferrin, the 7-mer sequence and the 12-mer sequence all bind unique sites on the hTfR, since they each failed to significantly compete with each other for hTfR binding. This finding suggests further advantages for use of these peptides for transduction of therapeutic ligands, since there is no disruption of transferrin's delivery of iron to cells.

Due to the characteristics and expression pattern of the hTfR, ligands specific for this receptor may be used as targeting agents with antigen as well as diagnostic agents such as imaging agents or radioisotopes. It has been shown that early endosomes are essential for the proper endocytosis, sorting and presentation of antigen by major histocompatibility class II. The targeting of antigens to the hTfR enhances antigen entry into the endocytic pathway and boosts antigen presentation.

It is possible to conjugate the peptides of the invention to liposomes or viral vectors containing active agents such as chemotherapeutics. (See Eavarone, et al, "Targeted Drug Delivery to C6 Glioma by Transferrin-coupled Liposomes", *Proceedings of the World Biomaterials Congress* 2000, (John Wiley and Sons, Inc.) (2000)). Alternatively, chemotherapeutics may be conjugated directly with the peptides of the invention for targeting agents to transferrin receptor-rich cells. Because the peptides of the invention do not interfere with binding of human transferrin to the hTfR, different agents may be administered wherein one conjugate targets the hTfR uses transferrin as the targeting agent and another conjugate targets the hTfR using a peptide of the invention as a targeting agent.

EXAMPLE 7

Transferrin receptor binding peptide sequences to adenovirus proteins in accord with the teachings of U.S. Pat. No. 6,312,699, which is incorporated herein by reference in its entirety. As described in example 2 of U.S. Pat. No. 6,312, 699, short peptide ligands such as HAIYPRH (Seq. ID No. 1) and THRPPMWSPVWP (Seq. ID No. 2) are fused onto the carboxyl-terminus of the adenovirus fiber protein. Oligonucleotides encoding these amino acid sequences are designed and synthesized and annealed together for cloning into the unique BamHI restriction endonuclease cleavage site in plasmid pTKgpt-3S (cited in example 2 of U.S. Pat. No. 6,312,699). Examples of such oligonucleotides are:

sequences into plasmid pTKgpt-3S, using synthetic oligonucleotides as in example 4 of the cited patent.

EXAMPLE 8

The Tf receptor binding peptides can be used to enhance antigen delivery in antigen-presenting cells. These peptide sequences are applied to increase the potency of vaccines, since antigen-presenting cells often take up the antigens contained in vaccines poorly. To enhance antigen delivery and, therefore, antibody and cytotoxic T cell responses, these peptides are chemically coupled to the antigen of interest or prepared as a recombinant protein that contains these Tf receptor-binding peptides. For preparation of the recombinant antigen containing the Tf receptor binding peptide, coupling is accomplished using standard recombinant DNA techniques as in other examples provided (for example, fusions of HAIYPRH (Seq. ID No. 1) and THRPPMWSPVWP (Seq. ID No. 2) to GFP or adenovirus fiber proteins.) The recombinant proteins can be expressed in any number of protein expression systems including bacterial, baculoviral, and mammalian expression systems.

For chemical conjugation of the Tf receptor binding peptides, the peptides are coupled using chemical crosslinkers such as succinimidyl 4-(N-maleimidomethyl) cyclohexane-1-carboxylate (SMCC; Piece Chem. Co., Rockford, Ill.). Obviously, any chemical crosslinker could be used for this purpose. In our applications, we have coupled 10 mg of antigen to a 5 to 30-fold molar excess of SMCC in 50 mM Hepes buffer (pH 7.4) for 1 h at room temperature.

EXAMPLE 9

SMCC-modified antigen is purified by gel filtration to remove the unbound crosslinker. Using this particular crosslinker, peptides are prepared with an amino-terminal linker sequence with a cysteine residue followed by a nonspecific linker sequence (glycine-proline-glycine) to

```
For HAIYPRH (Seq ID No. 1)
Sense:      5' GA TCC CAT GCG ATC TAT CCG CGC CAT TAA 3'           (Seq. ID No. 10)

Antisense: 5'  G ATC TTA ATG GCG CGG ATA GAT CGC ATG 3'            (Seq. ID No. 11)

For THRPPMWSPVWP (Seq ID No. 2)
Sense:                                                             5' GA TCC ACC CAC CGC CCG
                                                                   CCG ATG TGG AGC CCG GTG
                                                                   TGG CCG TAA    3'(Seq. ID
                                                                   No. 12)

Antisense:                                                         5' G ATC TTA CGG CCA CAC
                                                                   CGG GCT CCA CAT CGG CGG
                                                                   GCG GTG GGT G 3'(Seq. ID
                                                                   No. 13)
```

These oligonucleotides are designed with BamHI cohesive ends that can be cloned into the BamHI cleavage site developed in Example 2 of U.S. Pat. No. 6,312,699. The specific amino acid sequence added to fiber in Example 2 was designed to extend the new transferrin receptor-binding ligand away from the bulk of the fiber protein, increasing its accessibility to the new receptor molecule. The fiber protein, modified to include a linker and a ligand, could still form a trimer.

The non-viral ligands can be attached to the carboxyl terminus of the fiber protein via a peptide linker by expression of a genetically engineered nucleic acid sequence encoding the fiber protein, linker, and ligand. Alternatively, one could use PCR mutagenesis to introduce these two facilitate the coupling reaction. (The leader sequence can change depending on the nature of the crosslinker.) After the leader sequence, the 7- or 12-residue Tf receptor binding peptide is attached. The peptides are added to SMCC-modified antigens at same molar ratio as is used with the cross-linker. The reactions are incubated overnight at room temperature.

Reaction products are separated by gel filtration and the number of cross-linkers and/or peptides coupled to the antigen is determined by MALDI-TOF mass spectrometry. These Tf receptor binding peptide-modified antigens can then be used as a vaccine using standard vaccination protocols.

The advantage of the peptide-coupled antigens is that substantially less antigen will be required for inducing antibody-based responses. Since a number of peptides can be coupled to each antigen molecule, antigenic responses should be dramatically enhanced.

EXAMPLE 10

The peptides of the invention may also be coupled with chemotherapeutic agents. Using 2 equivalents of either peptide HAIYPRH (Seq. ID No. 1) or THRPPMWSPVWP (Seq. ID No. 2) or a combination of the two, to one equivalent of methotrexate the peptides of the invention are coupled to methotrexate using the methods of examples 8 and 9. The resulting product is formulated in buffered saline and administered to the patient in sufficient amount to provide a concentration of 0.3 to 5 μM in the serum when administred intravenously.

EXAMPLE 11

The methotrexate bound to the peptides of the invention is prepared as in example 10. However, the methotrexate bound to the peptides is then formulated in liposomal form for intravenous administration. Liposomal compositions may also be administred by mouth or directly to the affected tissue.

Examples of other antineoplastic agents that might be conjugated to the peptides of the invention, either directly or through conjugation to or incorporation in liposomes containing the sequences of the invention, such liposomes containing antineoplastic agents which may be bound to the peptides of the invention, to target cells rich in human transferrin receptors include (but are not limited to) cisplatin, nitrogen mustards (including chlorambucil), ethylenimines, methylmelamines, nitrosoureas (including carmustin, lomustine, etc.) and doxorubicin. The antineoplastic agents would be administered in accord with the methods usually used for the particular agent and disease. However, because of the selective targetting of the agent by the peptides, lower dosage is required. (The lowering of dosage of the antineoplastic agent can be as much as 80%.) Furthermore, because the over-all dosage of the neoplastic agent can be decreased, the active agent can be administered for a longer period of time and more frequently than when the non-targetting agent is employed.

The compositions with the peptides bound to antigens or antineoplastic agents may be administered directly to the involved tissues. For example, in cases of maligancy of the respiratory tract, the agents may be administred by inhalation. In treating maligancies of the brain or spinal cord, the agents may be administered intrathecally. For oral administration, the peptide-bound agents may be administred in enteric coated dosage forms to prevent destruction in the stomach.

What we claim is:

1. A composition of matter comprising a purified peptide containing the sequence THRPPMWSPVWP (Seq. ID No. 2).

2. A composition comprising at least one peptide containing the sequence (Seq. ID No. 2) wherein said peptide is fused to a protein or another peptide.

3. A composition of claim 2 wherein said sequence containing the sequence THRPPMWSPVWP (Seq. ID No. 2) is fused to a chemotherapeutic agent.

4. A composition of claim 2 wherein said sequence containing the sequence THRPPMWSPVWP (Seq. ID No. 2) is fused to an imaging agent.

5. A composition of claim 4 wherein said sequence containing the sequence THRPPMWSPVWP (Seq. ID No. 2) is fused to a fluorescing agent.

6. A composition of claim 2 wherein said sequence containing the sequence THRPPMWSPVWP (Seq. ID No. 2) is fused to an antigen.

7. A method of targeting an active agent to the human transferrin receptor by administration of said agent fused to a sequence containing the sequence THRPPMWSPVWP (Seq. ID No. 2) to a human subject.

* * * * *

SEQUENCE LISTING (1) GENERAL INFORMATION:

(iii) NUMBER OF SEQUENCES: 14

(2) INFORMATION FOR SEQ ID NO: 1:

(i) SEQUENCE CHARACTERISTICS:
      (A) LENGTH: 7 amino acids
      (B) TYPE: amino acid
      (C) STRANDEDNESS: single
      (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 1:

His Ala Ile Tyr Pro Arg His
1              5

(2) INFORMATION FOR SEQ ID NO: 2:

(i) SEQUENCE CHARACTERISTICS:
      (A) LENGTH: 12 amino acids
      (B) TYPE: amino acid
      (C) STRANDEDNESS: single
      (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 2:

```
Thr His Arg Pro Pro Met Trp Ser Pro Val Trp Pro
1               5                   10
```

(2) INFORMATION FOR SEQ ID NO: 3:

(i) SEQUENCE CHARACTERISTICS:
        (A) LENGTH: 7 amino acids
        (B) TYPE: amino acid
        (C) STRANDEDNESS: single
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 3:

```
Ile Arg His Pro His Tyr Ala
1               5
```

(2) INFORMATION FOR SEQ ID NO: 4:

(i) SEQUENCE CHARACTERISTICS:
        (A) LENGTH: 12 amino acids
        (B) TYPE: amino acid
        (C) STRANDEDNESS: single
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 4:

```
Pro Trp Arg Pro Ser His Pro Val Trp Met Pro Thr
1               5                   10
```

(2) INFORMATION FOR SEQ ID NO: 5:

(i) SEQUENCE CHARACTERISTICS:
        (A) LENGTH: 18 base pairs
        (B) TYPE: nucleic acid
        (C) STRANDEDNESS: single
        (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO: 5:

```
TGGGATTTTG CTAAAAAC                                               18
```

(2) INFORMATION FOR SEQ ID NO: 6:

(i) SEQUENCE CHARACTERISTICS:
        (A) LENGTH: 22 base pairs
        (B) TYPE: nucleic acid
        (C) STRANDEDNESS: single
        (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO: 6:

GTATGGGATT TTGCTAAACA AC                                          22

(2) INFORMATION FOR SEQ ID NO: 7:

(i) SEQUENCE CHARACTERISTICS:
        (A) LENGTH: 28 base pairs
        (B) TYPE: nucleic acid
        (C) STRANDEDNESS: single
        (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO: 7:

TCTAGATCTG ATGAGTAAAG GAGAAGAA                                    28

(2) INFORMATION FOR SEQ ID NO: 8:

(i) SEQUENCE CHARACTERISTICS:
        (A) LENGTH: 54 base pairs
        (B) TYPE: nucleic acid
        (C) STRANDEDNESS: single
        (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO: 8:

TTAAAGCTTT TAATGGCGCG GATAGATCGC ATGTTTGTAG AGCTCATCCA TGCC        54

(2) INFORMATION FOR SEQ ID NO: 9:

(i) SEQUENCE CHARACTERISTICS:
        (A) LENGTH: 68 base pairs
        (B) TYPE: nucleic acid
        (C) STRANDEDNESS: single
        (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO: 9:

TAAAGCTTTT ACGGCCACAC CGGGCTCCAC ATCGGCGGGC GGTGGGTTTT GTAGAGCTCA  60

TCCATGCC                                                          68

(2) INFORMATION FOR SEQ ID NO: 10:

(i) SEQUENCE CHARACTERISTICS:
        (A) LENGTH: 29 base pairs
        (B) TYPE: nucleic acid
        (C) STRANDEDNESS: single
        (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO: 10:

GATCCCATGC GATCTATCCG CGCCATTAA                                         29

(2) INFORMATION FOR SEQ ID NO: 11:

(i) SEQUENCE CHARACTERISTICS:
        (A) LENGTH: 29 base pairs
        (B) TYPE: nucleic acid
        (C) STRANDEDNESS: single
        (D) TOPOLOGY: unknown (ii) MOLECULE TYPE: DNA (genomic)

(iii) HYPOTHETICAL: NO (iv) ANTI-SENSE: YES (xi) SEQUENCE DESCRIPTION: SEQ ID NO: 11:

GATCTTAATG GCGCGGATAG ATCGCATGG                                         29

(2) INFORMATION FOR SEQ ID NO: 12:

(i) SEQUENCE CHARACTERISTICS:
        (A) LENGTH: 44 base pairs
        (B) TYPE: nucleic acid
        (C) STRANDEDNESS: single
        (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO: 12:

GATCCACCCA CCGCCCGCCG ATGTGGAGCC CGGTGTGGCC GTAA                         44

(2) INFORMATION FOR SEQ ID NO: 13:

(i) SEQUENCE CHARACTERISTICS:
        (A) LENGTH: 44 base pairs
        (B) TYPE: nucleic acid
        (C) STRANDEDNESS: single
        (D) TOPOLOGY: unknown (ii) MOLECULE TYPE: DNA (genomic)

(iii) HYPOTHETICAL: NO (iv) ANTI-SENSE: YES (xi) SEQUENCE DESCRIPTION: SEQ ID NO: 13:

GATCTTACGG CCACACCGGG CTCCACATCG GCGGGCGGTG GGTG                         44

(2) INFORMATION FOR SEQ ID NO: 14:

(i) SEQUENCE CHARACTERISTICS:
        (A) LENGTH: 7 amino acids
        (B) TYPE: amino acid
        (C) STRANDEDNESS: single
        (D) TOPOLOGY: unknown (ii) MOLECULE TYPE: peptide (iii) HYPOTHETICAL: NO (iv) ANTI-SENSE: NO

```
        -continued
    (v) FRAGMENT TYPE: internal (xi) SEQUENCE DESCRIPTION: SEQ ID NO: 14:

His Ala Ile Tyr Pro Asn His
1               5
```